United States Patent
Artois et al.

(10) Patent No.: US 7,144,703 B2
(45) Date of Patent: Dec. 5, 2006

(54) COMPOSITION

(75) Inventors: Claude Artois, Rhode-St-Genese (BE); Michael J Clark, Glabay (BE); Stefan Gabriel Jozef Thoelen, St Gilles (BE); Clothilde Thiriart, Brussels (BE)

(73) Assignee: SmithKline Beecham Biologicals, s.a., Rixensart (BE)

( * ) Notice: Subject to any disclaimer, the term of this patent is extended or adjusted under 35 U.S.C. 154(b) by 0 days.

(21) Appl. No.: 10/883,126

(22) Filed: Jul. 1, 2004

(65) Prior Publication Data

US 2004/0241193 A1 Dec. 2, 2004

Related U.S. Application Data

(63) Continuation of application No. 10/223,801, filed on Aug. 20, 2002, now abandoned, which is a continuation of application No. 09/674,397, filed as application No. PCT/EP99/03024 on Apr. 27, 1999, now abandoned.

(30) Foreign Application Priority Data

May 1, 1998 (GB) .................................. 9809507.8

(51) Int. Cl.
*C12Q 1/68* (2006.01)
(52) U.S. Cl. ........................................... 435/6; 435/7.1
(58) Field of Classification Search .................... 435/6, 435/235.1, 325, 7.1, 69.1
See application file for complete search history.

(56) References Cited

FOREIGN PATENT DOCUMENTS

| WO | WO 93/24148 | 12/1993 |
|----|-------------|---------|
| WO | WO 96/26741 | 9/1996  |

OTHER PUBLICATIONS

Ambrosch et al., "Clinical and Immunological Investigation of a New Combined Hepatitis A and Hepatitis B Vaccine", *Journal of Medical Virology*, 44(4): 452-456 (1994).
Murphy et al., Fields Virology, Chapter 19, 2nd Edition, pp. 480-482 (1994).
Green et al., Israel Journal of Medical Sciences, vol. 30(5-6), pp. 485-488 (1994).
Frey, et al. "Interference of Antibody Production to Hepatitis B Surface Antigen in a Combination Hepatitis A/Hepatitis B Vaccine" *The Journal of Infectious Diseases* 1999:180 pp. 2018-2022.

*Primary Examiner*—Ali R. Salimi
(74) *Attorney, Agent, or Firm*—Jason C. Fedon; Edward R. Gimmi; Charles M. Kinzig

(57) ABSTRACT

Novel vaccine compositions are provided comprising a hepatitis B antigen formulated with aluminium phosphate. The vaccine compositions may additionally contain an inactivated hepatitis A virus, aluminium hydroxide and formol. The combined hepatitis A and B vaccine formulations can, if desired, be administered to human subjects in a 2 dose regimen. Suitable formulations are illustrated.

8 Claims, No Drawings

COMPOSITION

CROSS REFERENCES TO RELATED APPLICATIONS

This application is a continuation of application Ser. No. 10/223,801, filed Aug. 20, 2002, now abandoned, which is a continuation of application Ser. No. 09/674,397, filed Oct. 31, 2000, now abandoned, which is a 371 of International Application No. PCT/EP99/03024, filed Apr. 27, 1999.

Vaccines for the prophylaxis of hepatitis A and hepatitis B infections are well known. For example the vaccine Engerix-B (Trade Mark) from SmithKline Beecham Biologicals is used to prevent Hepatitis B. This vaccine comprises hepatitis B surface antigen (specifically the 226 amino acid S-antigen described in Harford et al. in Postgraduate Medical Journal, 1987, 63 (Suppl. 2), 65–70) and is formulated using aluminium hydroxide as adjuvant. The vaccine Havrix (Trade Mark), also from SmithKline Beecham Biologicals can be used to prevent hepatitis A infections and is also formulated with aluminium hydroxide as adjuvant. This vaccine comprises an attenuated strain of the HM-175 Hepatitis A virus inactivated with formol (formaldehyde); see Andre et al [Prog Med. Virol. 1990, vol 37; p 72–95]. The vaccine Twinrix (Trade Mark) which is a combination of the above hepatitis A and hepatitis B antigens may be used to protect against hepatitis A and hepatitis B simultaneously.

European patent 0 339 667 (Chemo Sero) describes the general concept of combining a hepatitis A antigen and a hepatitis B antigen to make a combination vaccine. In that specification it is stated that the adjuvant which is used is not critical: it must only be capable of enhancing the immune activity to a desired extent and not cause any side-effects. It is stated that aluminium gel may be used, in particular aluminium hydroxide gel and aluminium phosphate gel.

PCT application WO 93/24148 (SmithKline Beecham) describes the preparation of vaccines comprising hepatitis B surface antigen in which aluminium phosphate is used as adjuvant. Multivalent combination vaccines which may optionally contain a hepatitis A antigen, are described. The use of formol is not disclosed.

European Patent Number 0 633 784 (SmithKline Beecham) describes novel vaccine formulations comprising a hepatitis B component, particularly hepatitis B surface antigen, in combination with aluminium phosphate, and 3 de-O-acylated monophosphoryl lipid A.

It has now been surprisingly found that vaccines comprising hepatitis B and/or hepatitis A antigens give exceptionally good results if the vaccine is formulated in a specific manner.

Using vaccine formulations according to the invention, it is possible to administer the vaccines in a 2 dose, rather than a 3 dose, regimen.

In a first aspect of the invention, there is provided an aqueous vaccine composition comprising hepatitis B surface antigen which is formulated with aluminium phosphate as adjuvant, the concentration of aluminium phosphate being selected such that there is a ratio of 0.015–0.1 mg aluminium phosphate per ug hepatitis B surface antigen.

Preferably the ratio is in the range 0.02 to 0.08 mg aluminium phosphate per µg HBsAg.

In a further aspect of the invention an inactivated hepatitis A virus (HAV) may optionally be added to the formulation of the invention, providing a combined hepatitis A plus B vaccine which may be administered in a 2 dose schedule.

The hepatitis A antigen is preferably the HM-175 strain used in the commercial product Havrix (SmithKline Beecham Biologicals).

The concentration of hepatitis A antigen in the vaccine formulation of the invention is preferably about 720–2880 EU units per ml. For the definition of EU units see Andre et al (1990) loc cit.

The compositions of the invention which comprise HAV may additionally comprise aluminium hydroxide, the total amount of aluminium hydroxide generally being 0.05–0.10 mg per ml.

The total amount of aluminium salt per 0.5 or 1 ml dose is normally in the range 0.4–1.0 mg.

In the vaccine composition of the invention it is advantageous to add formol (formaldehyde) such that the formol concentration is 10–200 µg per ml.

Preferably the formol concentration is about 20–160 µg per ml.

Normally the hepatitis B antigen will be hepatitis B surface antigen (HBsAg). The preparation of Hepatitis B surface antigen (HBsAg) is well documented. See for example, Harford et al in *Develop. Biol. Standard* 54, page 125 (1983), Gregg et al in *Biotechnology*, 5, page 479 (1987), EP-A-0 226 846, EP-A-0 299 108 and references therein.

As used herein the expression 'Hepatitis B surface antigen' or 'HBsAg' includes any HBsAg antigen or fragment thereof displaying the antigenicity of HBV surface antigen. It will be understood that in addition to the 226 amino acid sequence of the HBsAg S antigen (see Tiollais et al, Nature, 317, 489 (1985) and references therein) HBsAg as herein described may, if desired, contain all or part of a pre-S sequence as described in the above references and in EP-A-0 278 940. HBsAg as herein described can also refer to variants, for example the 'escape mutant' described in WO 91/14703. In a further aspect the HBsAg may comprise a protein described as SL* in European Patent Application Number 0 414 374, that is to say a protein, the amino acid sequence of which consists of parts of the amino acid sequence of the hepatitis B virus large (L) protein (ad or ay subtype), characterised in that the amino acid sequence of the protein consists of either:

(a) residues 12–52, followed by residues 133–145, followed by residues 175–400 of the said L protein; or
(b) residue 12, followed by residues 14–52, followed by residues 133–145, followed by residues 175–400 of the said L protein.

HBsAg may also refer to polypeptides described in EP 0 198 474 or EP 0 304 578.

Normally the HBsAg will be in particle form. It may comprise S protein alone or may be as composite particles, for example (L*,S) wherein L* is as defined above and S denotes the S-protein of hepatitis B surface antigen.

Preferably the HBsAg will be adsorbed on aluminium phosphate as described in WO93/24148.

Preferably the hepatitis B antigen is HBsAg S-antigen as used in the commercial product Engerix-B (SmithKline Beecham Biologicals).

The vaccine formulations of the present invention will contain an immunoprotective quantity of the antigens and may be prepared by conventional techniques. Vaccine preparation is generally described in New Trends and Developments in Vaccines, edited by Voller et al., University Park Press, Baltimore, Md., U.S.A. 1978. Encapsulation within liposomes is described, for example, by Fullerton, U.S. Pat. No. 4,235,877. Conjugation of proteins to macromolecules is disclosed, for example, by Likhite, U.S. Pat. No. 4,372,945 and by Armor et al., U.S. Pat. No. 4,474,757.

The vaccine compositions of the invention are preferably administered in a 0, 6 month schedule, that is to say a first dose at 0 months and a second dose at 6 months.

The vaccine compositions of the present invention are especially appropriate for adults and are also appropriate for administration to adolescents and children.

The following examples illustrate but do not limit the invention.

EXAMPLES

Example 1

Specific Formulations

Specific formulations within the scope of the invention include the following:
a) A vaccine composition for administration to adults which comprises:
40 μg HBsAg
1440 EU HAV
0.85 mg Aluminium salt (0.8 mg aluminium phosphate plus 0.05 mg aluminium hydroxide)
20 μg formol
in a 0.5 ml dose
b) A vaccine composition for administration to adults which comprises:
40 μg HBsAg
1440 EU HAV
0.85 mg Aluminium salt (0.8 mg aluminium phosphate plus 0.05 mg aluminium hydroxide)
20 μg formol
in a 1.0 ml dose
c) A vaccine composition for administration to adolescents and/or children which comprises:
20 μg HBsAg
720 EU HAV
0.45 mg Aluminium salt (0.4 mg aluminium phosphate plus 0.05 mg aluminium hydroxide)
80 μg formol
in a 1 ml dose
d) A vaccine composition for administration to adolescents and/or children which comprises:
20 μg HBsAg
720 EU HAV
0.45 mg Aluminium salt (0.4 mg aluminium phosphate plus 0.05 mg aluminium hydroxide)
80 μg formol
in a 0.5 ml dose

Example 2

Study 'HAB 054'

2.1 One group of 47 healthy adult individuals was vaccinated with a vaccine composition (1 ml volume) containing:
1440 EU HAV antigen
40 μg HBsAg (S-antigen)
0.8 mg $AlPO_4$
0.05 mg Aluminium hydroxide
20 μg/ml formol.

This is abbreviated in the tables below to '1440/NF40'

2.2 One group of 47 healthy adult individuals was vaccinated:
a) in one arm with a vaccine composition containing 40 μg of HBsAg formulated with 0.8 mg $AlPO_4$, 20 μg/ml formol (hereinafter this composition is abbreviated to 'NF 40') in a 1 ml dose; and
b) in the opposite arm with HAVRIX 1440 containing 1440 EU HAV antigen on 0.5 mg Aluminium hydroxide and containing 20 μg/ml formol in a 1 ml dose.

The immunization schedule for HAB 054 was 0,6 (i.e. doses administered at month 0 and month 6).

The Hepatitis B serological results at months 2,6 and 7 (seroconversion (SC), seroprotection (SP) and geometric mean titre (GMT)) were unexpectedly high as compared to historical results obtained in another study (HBV NF 021) in which volunteers of the same age group were included.

Study HBV NF 021 (see Table 1) included three groups:
Group 1: Vaccinated with a formulation containing 40 μg of HBsAg on 0.5 μg $AlPO_4$ in 0.5 ml volume without formol, schedule 0, 6 months (this is abbreviated in the table to NF 40 μg, 0, 6M)
Group 2: Vaccinated with a formulation containing 20 μg of HBsAg on 0.5 μg $AlPO_4$ in 0.5 ml volume without formol, schedule 0, 6 months (this is abbreviated in the table to NF 20 μg, 0, 6M)
Group 3: Vaccinated with an Engerix B formulation (20 μg) using a classical 3 dose immunization schedule of 0, 1, 6 months (third row of data in Table 1)

Results

1) In study HBV NF 021, Hepatitis B serological results at month 7 in groups 1 and 2 were not satisfactory as compared to group 3 (lower SC, SP and GMT+/−1/3 (500 to 600) of the levels obtained after three doses of Engerix-B (1500)).

2) In study HAB 054, the titres obtained after 2 doses of vaccine were of the same order of magnitude as those that would be obtained following three doses of Engerix B.

TABLE 1

| | HBV - NF 021 STUDY | | | | | | | | |
|---|---|---|---|---|---|---|---|---|---|
| | Serconversion % | | | Seroprotection % | | | Geometric Mean Titre | | |
| | Month 2 | Month 7 | Month 8 | Month 2 | Month 7 | Month 8 | Month 2 | Month 7 | Month 8 |
| NF 40 μg (0.6 M) | 50 | 98 | 98 | 16 | 93 | 96 | 5 | 883 | 683 |
| NF 20 μg (0.6 M) | 42 | 93 | 98 | 6 | 91 | 89 | 3 | 727 | 510 |
| Engerix B 20 μg (0.1.6 M) | 74 | 100 | 100 | 50 | 100 | 100 | 23 | 1579 | 1550 |

TABLE 2

HAB 054 study
HAB 2-dose program in adults (0, 6month schedule)
N = 94

| HAB 054 | Seroconversion (in %) Anti-HBs | | | | |
|---|---|---|---|---|---|
| | month 2 | month 6 | month 7 | month 9 | month 12 |
| HAV 1440/NF40 | 75 | 85 | 100 | 100 | 100 |
| NF 40 (Havrix 1440 in other arm) | 80 | 87 | 96 | 97 | 97 |

HAV 1440/NF40: contains 0.85 mg Al salts  0.8 Al PO$_4$ 20 µg formol in 1 ml  0.05 Al (OH)$_3$
NF 40: contains 0.8 mg Al PO$_4$  20 µg formol in 1 ml

TABLE 3

HAB 054 study
HAB 2-dose program in adults (0, 6 month schedule)
N = 94

| HAB 054 | Seroprotection (in %) Anti-HBs | | | | |
|---|---|---|---|---|---|
| | month 2 | month 6 | month 7 | month 9 | month 12 |
| HAV 1440/NF40 | 36 | 62 | 100 | 100 | 100 |
| NF 40 (Havrix 1440 in other arm) | 33 | 57 | 96 | 97 | 90 |

HAV 1440/NF40 contains 0.85 mg Al salts  0.8 Al PO$_4$ 20 µg formol in 1 ml  0.05 Al (OH)$_3$
NF 40: contains 0.8 mg Al PO$_4$  20 µg formol in 1 ml

TABLE 4

HAB 054 study
HAB 2-dose program in adults (0, 6month schedule)
N = 94

| ANTI-HBs | geometric mean titre - anti-HBs | | | | |
|---|---|---|---|---|---|
| | month 2 | month 6 | month 7 | month 9 | month 12 |
| HAV 1440/NF40 | 8.5 | 19 | 2286 | 1006 | 632 |
| NF 40 (Havrix 1440 in other arm) | 8.8 | 18 | 1865 | 1107 | 484 |

HAV 1440/NF40: contains 0.85 mg Al salts  0.8 Al PO$_4$ 20 µg formol in 1 ml  0.05 Al(OH)$_3$
NF 40: contains 0.8 mg Al PO$_4$  20 µg formal in 1 ml

TABLE 5

HAB 054 study
HAB 2-dose program in adults (0, 6 month schedule)
N = 94

| HAB 054 | S+ % - HAV | | | | |
|---|---|---|---|---|---|
| | Day 15 | month 1 | month 6 | month 7 | month 9 | month 12 |
| HAV 1440/NF40 | 78 | 100 | 100 | 100 | 100 | 100 |
| NF 40 (Havrix 1440 in other arm) | 92 | 98 | 96 | 96 | 100 | 100 |

HAV 1440/NF40 contains 0.85 mg Al salts  0.8 Al PO$_4$ 20 µg formol in 1 ml  0.05 Al (OH)$_3$
NF 40: contains 0.8 mg AlPO$_4$  20 µg formol in 1 ml

TABLE 6

HAB 054 study
HAB 2-dose program in adults (0, 6 month schedule)
N = 94

| ANTI-HAV | Geometric mean titre - Anti-HAV | | | | | |
|---|---|---|---|---|---|---|
| | day 15 | month 1 | month 6 | month 7 | month 9 | month 12 |
| HAV 1440/NF40 | 337 | 803 | 324 | 10.393 | 7.408 | 4077 |
| NF 40 (Havrix 1440 in other arm) | 312 | 722 | 275 | 5.748 | 4.376 | 2882 |

HAV 1440/NF40: contains 0.85 mg Al salts  0.8 Al PO$_4$ 20 µg formol in 1 ml  0.05 Al (OH)$_3$
NF 40: contains 0.8 mg Al PO$_4$  20 µg formal in 1 ml Example 3

Studies 'HAB 063, HAB071 and HAB 075'
HAB 2 Dose Program in Adolescents Aged 11–18
3.1: Study HAB 063
Vaccine composition comprises:
720 HAV EU/20 µg HBs Ag
0.25 mg Al Salt
40 µg formol
In 0.5 ml dose
Results are shown in Table 7.

TABLE 7

HAB 063 study
HAB 2-dose program in adolescents aged 11–18 years
(0, 6 month schedule)
N = 52

| Antibody | PI (m1) | PI (m2) | PI (m6) | PII(m7) |
|---|---|---|---|---|
| Anti-HAV | | | | |
| S+ % | 100 | 96.2 | 96.2 | 100 |
| GMT (EL. U/ml) | 504 | 318 | 199 | 6874 |
| Anti-HBs | | | | |
| S+ % | 51.9 | 75 | 94.2 | 98.1 |
| Seroprotection rate % | 30.8 | 28.8 | 71.2 | 98.1 |
| GMT (mIU/ml) | 11 | 7 | 19 | 4110 |

3.2: Study HAB 071
Two groups were used in this study.
Vaccine composition group 1:
720 HAV EU/20 µg HBs Ag
0.425 mg Al Salt
40 µg formol
In 0.5 ml dose and at a schedule of 0, 6 months
Vaccine composition group 2 (Twinrix™ Junior):
360 HAV EU/10 µg HBsAg
0,225 mg Al Salt
40 µg formol In 0.5 ml dose and at a schedule of 0, 1, 6 months

TABLE 8

HAB 071 study

| High Dose HAB (Group 1) Schedule 0, 6 | PI (m1) n = 50 | PI (M2) n = 48 | PI (m6) n = 49 | PI (m7) n = 49 |
|---|---|---|---|---|
| Anti-HAV$^{antibodies}$ | | | | |
| S+ % | 100.0 | 100.0 | 100.0 | 100.0 |
| GMT (EL. U/ml) | 641 | 347 | 161 | 8151 |
| Anti-HBs$^{antibodies}$ | | | | |
| S+ % | 74.0 | 70.8 | 85.7 | 100.0 |
| Seroprotoection rate % | 40.0 | 27.1 | 57.1 | 100.0 |
| GMT (EL. U/ml) | 12 | 9 | 17 | 4212 |
| Twinrix ™ Junior(Group 2) Schedule 0, 1, 6 | PI (m1) n = 49 | PI (M2) n = 48 | PI (M2) n = 48 | PI (m7) n = 48 |
| Anti-HAV$^{antibodies}$ | | | | |
| S+ % | 95.9 | 100.0 | 97.9 | 100.0 |
| GMT (EL. U/ml) | 336 | 793 | 233 | 6394 |
| Anti-HBs$^{antibodies}$ | | | | |
| S+ % | 61.2 | 97.9 | 100.0 | 100.0 |
| Seroprotoection rate % | 36.7 | 83.3 | 97.9 | 100.0 |
| GMT (EL. U/ml) | 12 | 36 | 202 | 6330 |

3.3 Study HAB 075
Two groups were used in this study.
Vaccine composition group 1 (Twinrix™):
720 HAV EU/20 μg HBs Ag
0.45 mg Al Salt
80 μg formol
  In 1 ml dose and at a schedule of 0, 6 months
N=67
Vaccine composition group 2:
1440 HAV EU/40 μg HBs Ag
0.85 mg Al Salt
80 μg formol
  In 1 ml dose and at a schedule of 0, 6 months
N=55

TABLE 9

HAB 075 study

| Group | | | PI(m1) | PI(m2) | PI(m6) | PII(m7) |
|---|---|---|---|---|---|---|
| 1 | Anti-HAV | S+ % | 97.0 | 95.5 | 100.0 | 100.0 |
| | | GMT | 349 | 193 | 135 | 5646 |
| | Anti-HBs | S+ % | 62.7 | 74.6 | 95.5 | 100.0 |
| | | SP rate % | 22.4 | 32.8 | 61.2 | 100.0 |
| | | GMT | 6 | 6 | 13 | 3046 |
| 2 | Anti-HAV | S+ % | 100.0 | 100.0 | 100.0 | 100.0 |
| | | GMT | 533 | 318 | 249 | 9565 |
| | Anti-HBs | S+ % | 67.3 | 85.5 | 94.5 | 100.0 |
| | | SP rate % | 32.7 | 41.8 | 72.7 | 100.0 |
| | | GMT | 9 | 9 | 26 | 3497 |

Example 4

Study 'HAB 084'
  HAB 2 Dose Program in Adolescents Aged 12–15
  Two groups were used in this study.
  Vaccine composition group 1 (Twinrix™):
720 HAV EU/20 μg HBs Ag
0.45 mg Al Salt
80 μg formol
  In 1 ml dose and at a schedule of 0, 6 months
Vaccine composition group 2 (Twinrix™ Junior):
360 HAV EU/10 μg HBs Ag
0.225 mg Al Salt
40 μg formol
  In 0.5 ml dose and at a schedule of 0, 1, 6 months

TABLE 10

HAB 084 study

| Group | | | | | | |
|---|---|---|---|---|---|---|
| 1 (0, 6) | | | PI(m1) N = 142 | PI(m2) N = 142 | PI(m6) N = 142 | PII(m7) N = 142 |
| | Anti-HAV | S+ % | 99.3 | 100 | 100 | 100 |
| | | GMT | 348 | 244 | 178 | 5486 |
| | Anti-HBs | S+ % | 80.5 | 81 | 93 | 100 |
| | | SP rate % | 43 | 38 | 68 | 97.9 |
| | | GMT | 14 | 9 | 20 | 4948 |
| 2 (0, 1, 6) | | | PI(m1) N = 148 | PII(m2) N = 146 | PII(m6) N = 147 | PIII(m7) N = 147 |
| | Anti-HAV | S+ % | 93.2 | 99.3 | 99.3 | 100 |
| | | GMT | 227 | 548 | 298 | 4174 |
| | Anti-HBs | S+ % | 58.1 | 95.9 | 99.3 | 100 |
| | | SP rate % | 29.1 | 85.6 | 98 | 100 |
| | | GMT | 9 | 42 | 305 | 5054 |

Example 5

Study 'HAB 076'
  HAB 2 Dose Program in Children Aged 1–11 Years
  Vaccine composition comprises:
720 HAV EU/20 μg HBs Ag
0.45 mg Al Salt
80 μg formol
  In 1 ml dose at a schedule of 0, 1 month
  Results are shown in Table 11.

TABLE 11

HAB 076 study

| | | PI(m1) N = 194 | PI(m2) N = 201 | PI(m6) N = 197 | PII(m7) N = 199 |
|---|---|---|---|---|---|
| Anti-HAV | S+ % | 99.5 | 98.5 | 98 | 100 |
| | GMT | 434 | 293 | 193 | 11543 |
| Anti-HBs | S+ % | 72.7 | 89.1 | 93.9 | 100 |
| | SP rate % | 30.3 | 47.3 | 78.2 | 98.5 |
| | GMT | 8 | 11 | 34 | 8056 |

SUMMARY

The clinical results shown in the above examples clearly indicate that a satisfactory immune response is obtained, both for hepatitis A and hepatitis B after the full schedule, that is by Month 7, in children, adolescents and adults.

The invention claimed is:
  1. A method of inducing a seropositive antibody response against hepatitis A virus and hepatitis B virus and a seroprotective antibody response against hepatitis B virus in infants or adolescents, the method comprising administering two doses of a vaccine composition comprising hepatitis B surface antigen, aluminium phosphate, an inactivated hepatitis A virus, aluminium hydroxide, and formol.

2. The method of claim 1 wherein the vaccin comprises 10 to 200 micrograms per milliliter of formol.

3. The method of claim 1 wherein the concentration of inactivated hepatitis A virus is about 720 to 2880 EU per milliliter.

4. The method of claim 1 wherein the concentration of hepatitis B surface antigen is 20 to 40 micrograms per milliliter.

5. The method of claim 1 wherein the inactivated hepatitis A virus is derived from the HM-175 strain.

6. The method of claim 1 wherein the hepatitis B surface antigen is the S-antigen.

7. The method of claim 1 wherein a second dose of the vaccine composition is administered 1 month after administration of a first dose.

8. The method of claim 1 wherein a second dose of the vaccine composition is administered 6 months after administration of a first dose.

* * * * *